US006829551B2

(12) United States Patent
Von Der Hardt et al.

(10) Patent No.: US 6,829,551 B2
(45) Date of Patent: Dec. 7, 2004

(54) TEST DEVICE FOR FILTER SYSTEMS, METHOD FOR TESTING FILTER SYSTEMS, AND COMPUTER PROGRAM THEREFOR

(75) Inventors: Jochen Von Der Hardt, Goettingen (DE); Reinhard Baumfalk, Goettingen (DE); Oscar-Werner Reif, Hannover (DE); Juergen Van Den Boogaard, Coram, NY (US)

(73) Assignee: Sartorius AG, Goettingen (DE)

( * ) Notice: Subject to any disclaimer, the term of this patent is extended or adjusted under 35 U.S.C. 154(b) by 26 days.

(21) Appl. No.: 10/198,075

(22) Filed: Jul. 19, 2002

(65) Prior Publication Data

US 2003/0033106 A1 Feb. 13, 2003

(30) Foreign Application Priority Data

Jul. 19, 2001 (DE) .......................................... 101 35 295

(51) Int. Cl.[7] .............................................. G01L 23/00
(52) U.S. Cl. .................... 702/114; 73/168; 210/321.69; 210/348
(58) Field of Search ................................ 702/114, 113, 702/108; 73/38, 168, 40, 40.7; 210/636, 321.69, 90, 140, 143, 85, 359, 321.72, 348

(56) References Cited

U.S. PATENT DOCUMENTS 4,701,861 A * 10/1987 Kauke ......................... 700/266
4,881,176 A * 11/1989 Kononov ..................... 700/271
5,064,529 A * 11/1991 Hirayama et al. ............. 210/90
5,353,630 A * 10/1994 Soda et al. ..................... 73/38
5,762,804 A *  6/1998 Striefler ....................... 210/636
6,453,257 B1 *  9/2002 Juhasz ......................... 700/266

FOREIGN PATENT DOCUMENTS

| DE | 3917856 | 12/1989 |
| DE | 4413081 | 3/1995 |
| DE | 19725916 | 1/1999 |
| DE | 19858589 | 6/2000 |

OTHER PUBLICATIONS

J. Krueger, et al., "Maschinendiagnose ueber das Internet", ZWF 91 (1996) 12, pp. 604–606.

* cited by examiner

*Primary Examiner*—John Barlow
*Assistant Examiner*—Hien Vo
(74) *Attorney, Agent, or Firm*—Crowell & Moring LLP (57) ABSTRACT

A test device (10) for filter systems comprising at least two test units (14), a management unit (12) for managing and controlling the at least two test units (14), and signal links via a bi-directional or multi-directional network (16) between the management unit (12) and the at least two test units (14), particularly for transmitting test program instructions and test results. The invention further relates to a method for testing filter systems and a computer readable storage device with a computer program stored therein for testing filter systems.

21 Claims, 5 Drawing Sheets

TEST DEVICE FOR FILTER SYSTEMS, METHOD FOR TESTING FILTER SYSTEMS, AND COMPUTER PROGRAM THEREFOR

BACKGROUND OF THE INVENTION

The present invention relates to a test device for filter systems, a method for testing filter systems, and a computer readable storage device with a computer program for testing filter systems stored therein.

Test devices for filter systems are known in the art. They are used to test filter devices, particularly membrane filters, e.g., for filter quality.

Such a test device is described, for instance, in German patent no. DE 39 17 856 C2. The test device described in this patent comprises a splash-water-protected, plastic enclosure with an operator panel equipped with input keyboard, an LCD display, a printing device and, in the interior, at least a portion of the electronics. The lower part of the enclosure houses the pneumatic equipment and has a compressed gas inlet that is connected with a pneumatic source, a pressure outlet that is connected to the filter system to be tested, and a connection for temperature sensor lines. Testing a filter with such a test device is time consuming, however, since each filter to be tested must be measured separately.

SUMMARY OF THE INVENTION

Thus, an object of the invention is to provide an improved test device for filter systems.

A particular object of the invention is to provide a filter system test device which facilitates automated testing of multiple filter systems.

Another object of the invention is to provide a method for testing filter systems which enables improved testing.

A further object of the invention is to provide a computer readable storage device with a computer program for testing filter systems stored therein, to allow improved testing of filter systems.

These and other objects are achieved by the invention as described and claimed hereinafter.

According to the invention, a test device for filter systems is provided, wherein the test device for filter systems comprises:

at least two test units, each of which comprises:
a control unit for controlling the sequence of a test program or test program instructions for one or more filter devices,
a pneumatic unit controlled by the control unit, particularly for providing and measuring pressures;
a management unit for managing and controlling the at least two test units, wherein the management unit comprises:
an input device for user-specific inputs, and
an output device,
a processing unit for managing test programs or test program instructions and test results and for controlling the at least two test units, and
signal links via a bi-directional or multi-directional network between the management unit and the at least two test units, particularly for transmitting test program instructions and test results.

By providing at least two test units, which are managed by a common management unit, several filters can preferably be tested simultaneously. Furthermore, the costs of the test device can be reduced since only the device required for testing must be present in multiple units, whereas the device for managing the tests needs to be present only as a single unit.

The signal links via a bi-directional or multi-directional network between the management unit and the test unit can preferably comprise an Intranet or an Internet connection.

Communication between the management unit and the at least two test units is preferably provided as a master-slave configuration. In particular, the management unit performs the function of the master, which actively controls and manages the at least two test units, and the at least two test units are considered slaves, which assume a passive, executing function.

Preferably, the test unit further comprises a data processing unit for processing test program instructions and/or test results. By providing a data processing unit in the test unit, a portion of the required computing activity can be executed in the test unit to relieve or simplify the management unit.

The test unit preferably further comprises a storage unit for storing at least one test program instruction and/or the test results. This ensures simple access to data and instructions.

The input device of the management unit is preferably equipped with a keyboard and/or a touch screen. Providing a keyboard and/or a touch screen enables user-defined inputs, e.g., regarding the filter test.

The output device of the management unit is preferably equipped with a printer for printing out preferably the test parameters used and the test results obtained, and particularly also the certification results.

The management unit further comprises a display device, preferably a monitor. This display device is used to display, for example, the test parameters, the test results and/or the progression of a filter test.

In a preferred embodiment, the signal links between the management unit and the at least two test units comprise an electrical, optical, infrared and/or radio link.

The management unit can preferably manage the at least two test units essentially simultaneously. As a result, less time is required to test a filter system.

In a preferred embodiment, up to five test units are assigned to a management unit.

The invention furthermore provides a method for testing filter systems, particularly using a test device according to the invention or a preferred embodiment thereof, wherein the method comprises the following steps:

transmitting at least one test program instruction from the management unit to at least one of the at least two test units so as to cause the at least one test program instruction to be executed in the at least one test unit to which the test program was transmitted; and
recording the test results of the at least one test unit in the management unit.

Preferably, the management unit can essentially simultaneously communicate with the at least two test units.

The invention further provides a method for testing filter systems, particularly using a test device according to the invention or a preferred embodiment thereof, wherein the method comprises the following steps:

recording at least one test program instruction from the management unit out of a plurality of test instructions transmitted to at least one of the at least two test units;
executing the at least one test program instruction in the at least one test unit to which the test program was transmitted; and
transmitting the test results from the at least one test unit to the management unit.

Preferably, the method further comprises a step of causing the at least one test program instruction to be stored in one of the at least two test units.

In a preferred embodiment, the method further comprises a step of causing the test results to be stored, and preferably to be processed, in one of the at least two test units.

The invention further provides a computer readable storage device with a computer program for testing filter systems stored therein, which comprises program sections to execute a method according to the invention or a preferred embodiment thereof.

Other objects, features and advantages of the present invention will be apparent from the following description, which is provided by way of example.

BRIEF DESCRIPTION OF THE DRAWINGS

The invention will be described in further detail hereinafter with reference to illustrative preferred embodiments shown in the accompanying drawings, in which.

DETAILED DESCRIPTION OF PREFERRED EMBODIMENTS

Figure 1:
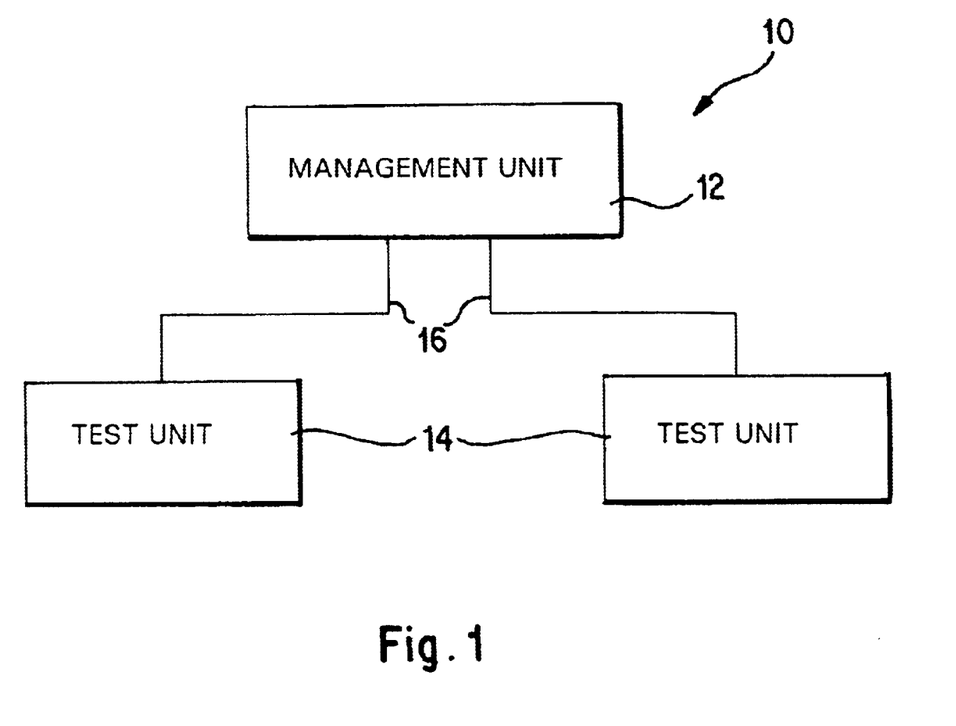
FIG. 1 is a schematic view of a test device for filter systems according to a preferred embodiment of the present invention.

FIG. 1 shows a test device 10 for filter systems according to a preferred embodiment of the present invention. This inventive test device 10 is used, for example, to test filters, e.g., filter cartridges, dead end filters with tubular, capillary or flat membranes, or filter systems 18 (which will be described in greater detail below).

The inventive test device 10 shown in FIG. 1 comprises a management unit 12 and two test units 14. It is also possible, however, to connect or have more than two test units 14 connected to management unit 12. In a preferred embodiment, up to five test units 14 can be connected to one management unit 12. The management unit 12 is connected to the test units 14 via a bi-directional or multi-directional network 16, particularly via the Internet or an Intranet. The bi-directional or multi-directional network 16 preferably comprises electrical or electromagnetic, optical, infrared, and/or radio links.

Figure 2:
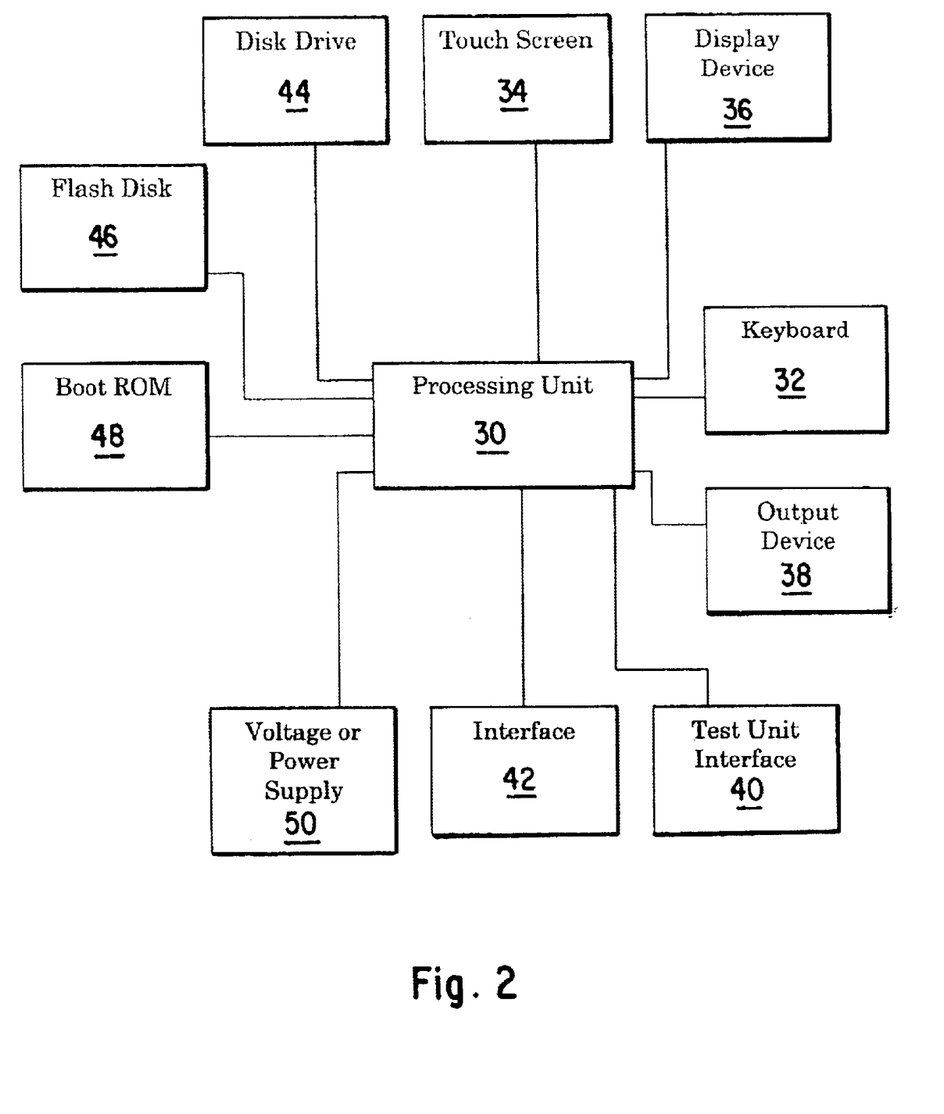
FIG. 2 is a schematic view of a management unit of the test device for filter systems according to a preferred embodiment of the present invention.

FIG. 2 is a schematic view of a management unit 12. The management unit 12 comprises a processing unit 30, which preferably includes a processor, particularly for managing test programs and/or test program instructions, and for controlling the at least two test units 14. Management unit 12 further comprises an input device for entering instructions to operate management unit 12, particularly to start/terminate test programs and/or evaluate/display test results. The input device can include a keyboard 32 and/or a touch screen 34. Management unit 12 further comprises a display device 36 and an output device 38, which preferably includes a printer. Management unit 12 further comprises an interface or a test unit interface 40 for connecting test units 14. The test unit interface 40 is preferably an RS485 interface. Other interfaces are also feasible, however. Via this test unit interface 40, management unit 12 can transmit preferably test program instructions to test unit 14 and receive test results from the test unit 14. Via an additional interface or PC interface 42, management unit 12 can be connected to an external computer, e.g., to import new versions of test software. Preferably, management unit 12 further comprises a floppy disk drive 44, a flash disk 46, and a boot ROM 48. Management unit 12 uses a voltage or power supply 50 for test unit 14.

Test units 14 are essentially mechanically, pneumatically and electrically self-contained functional units. To supply a test unit 14 with the fluids or pressures required for the corresponding tests, test unit 14 is preferably equipped with supply connections, which cannot be controlled directly by the user. They are completely remote-controlled by management unit 12 via test unit interface 40, which preferably may be an RS485 interface. Test units 14, by means of their electrical and pneumatic peripherals perform the actual filter test and a series of additional functions. The at least two test units 14 are preferably spatially or locally separated from one another and from management unit 12. However, an embodiment in which, for instance, a test unit 14 is integrated in management unit 12, or management unit 12 is mounted or attached to a plurality of test units 14, is also feasible.

Figure 3:
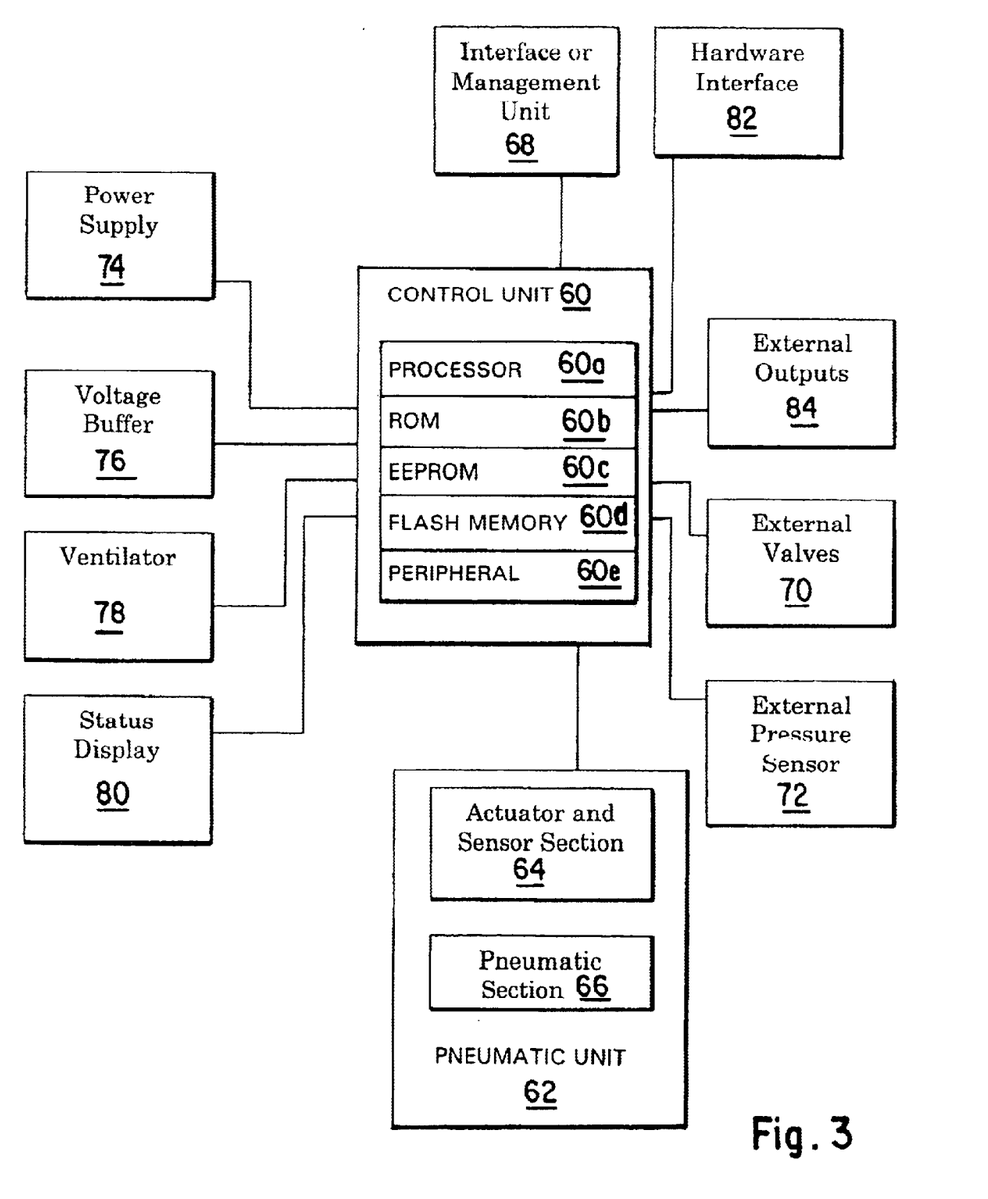
FIG. 3 is a schematic view of a test unit of the test device for filter systems according to a preferred embodiment of the present invention.

FIG. 3 shows a schematic view of a test unit 14. All test units 14 are essentially identical in their configuration. However, individual test units 14 can also be equipped with special devices to enable them to perform special tests. A preferred embodiment of a test unit 14 will now be described with reference to FIG. 3.

Test unit 14 comprises a control unit 60 for controlling the sequence of a test program or a test program instruction for one or more filter systems. Control unit 60 preferably comprises a processor 60a, a RAM 60b, an EEPROM 60c, a flash memory 60d, and a peripheral 60e. Control unit 60 can also comprise other suitable devices.

Test unit 14 is further equipped with a pneumatic unit 62. Pneumatic unit 62 preferably comprises an actuator and sensor section 64 and a pneumatic section 66. The actuator and sensor section 64 preferably comprises valves, proportional valves, temperature sensors and pressure sensors (not shown). The pneumatic section 66 preferably comprises pipes or lines, a manifold block with integrated valve recess and an internal reference tank (not shown). Furthermore, an external reference tank (not shown) can be connected to pneumatic unit 62.

Test unit 14 further comprises an interface or management unit interface 68, which corresponds to or is adapted to test unit interface 40 of management unit 12 and which is used to connect test unit 14 to management unit 12. In a preferred embodiment, if test unit interface 40 of management unit 12 is an RS485 interface, management unit interface 68 is preferably also an RS485 interface. Management unit interface 68 can be provided internally or externally on test unit 14.

Test unit 14 is further equipped with external valves 70 and an external pressure sensor 72. Preferably a power supply 74, a voltage buffer 76, a ventilator 78, and a status display 80, preferably with four light emitting diodes (not shown) are also provided in test unit 14. Furthermore, test unit 14 is preferably equipped with a hardware interface 82 and two additional external outputs 84.

The main task of test unit 14 is to use various methods to test the integrity of filters, preferably membrane filters. To this end, test unit 14 controls a number of the above-described valves and measures pressures and temperature.

Since test unit 14 has essentially no operator interface of its own (possibly only an emergency switch or the like), the activity of test unit 14 is completely controlled and observed through communication with management unit 12. Preferably, management unit 12 can essentially manage a plurality of test units 14 in parallel or simultaneously. Because a management unit 12 can be spatially separate from the at least two test units 14, it is essentially possible to test a plurality of filter systems 18 simultaneously, so that the time required for the filter tests can be reduced. On the other hand, the filter test of a plurality of filter systems 18 can be easily controlled from management unit 12, so that a test system with delocalized test units can be centrally controlled via management unit 12.

Figure 4:
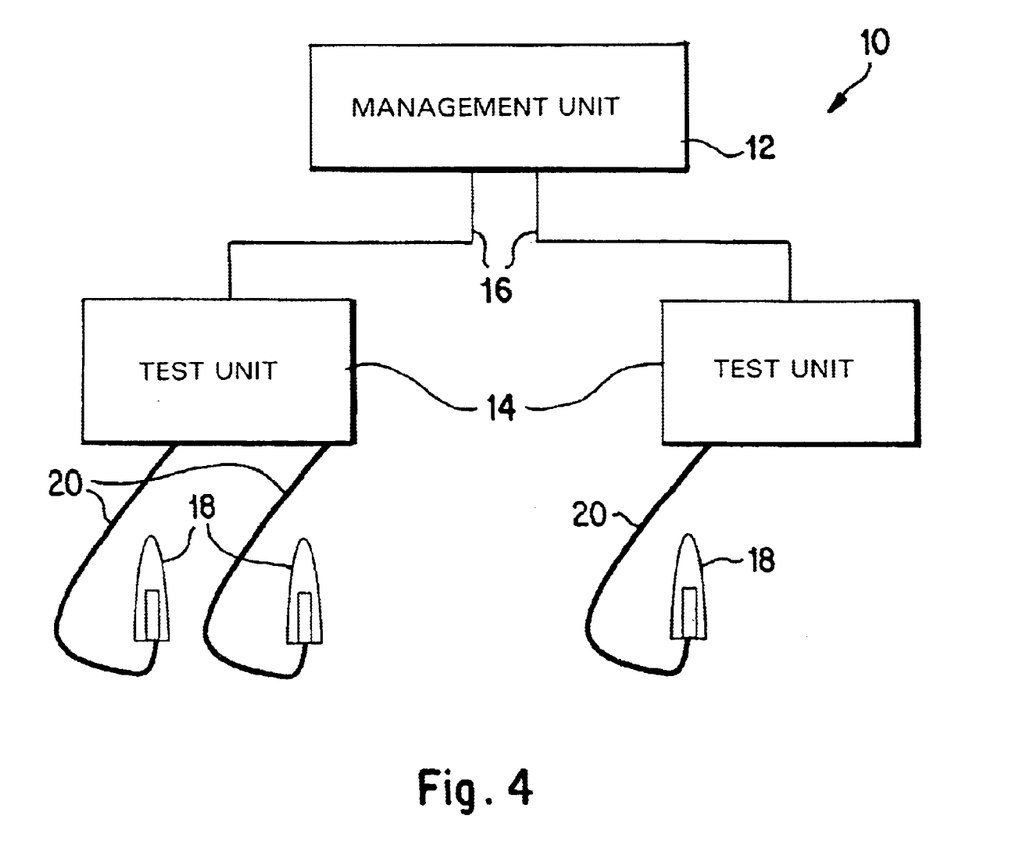
FIG. 4 is a schematic view of the test device for filter systems according to a preferred embodiment of the present invention when the filter systems to be tested are connected.

FIG. 4 schematically shows a test device 10 according to the present invention with filters or filter systems 18 connected via lines 20. Although FIG. 4 shows only two test units 14, more than two test units 14 can be connected to management unit 12 according to the invention. As may be seen from FIG. 4, one or more filters 18 can be connected to a test unit 14.

Figure 5:
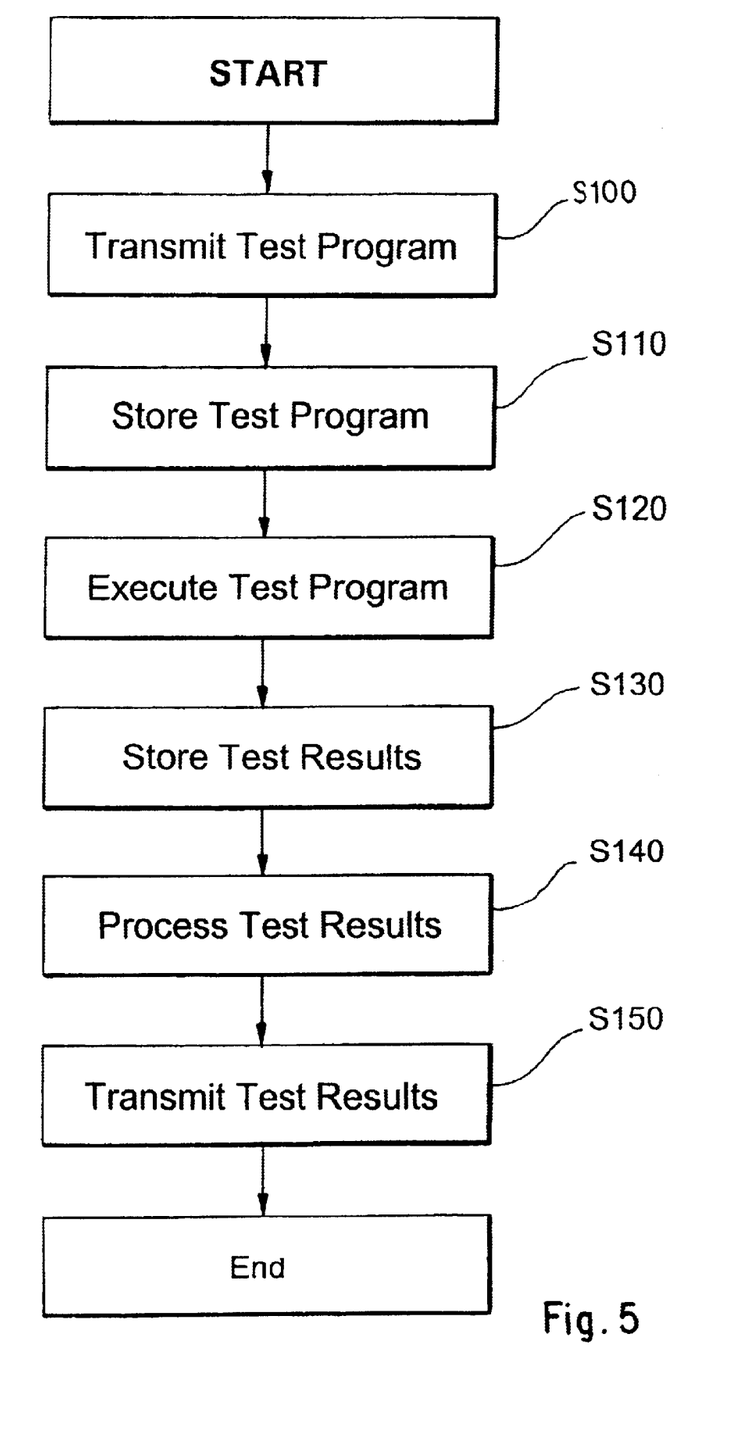
FIG. 5 is a flow chart showing the progression of a test procedure according to a preferred embodiment of the present invention.

FIG. 5 shows a flow chart illustrating the progression of a test procedure, i.e., a filter test, according to a preferred embodiment of the present invention.

A filter test according to procedure X with filter unit Y is referred to as a test program. This test program defines the procedure and the parameters for the filter test. A test program comprises at least one test program instruction. Test unit 14 can preferably load and execute a maximum of one such test program.

The sequence of a filter test will now be described by way of example.

First, management unit 12 transmits all information, i.e., the test program and/or the test program instruction, required for a filter test via the bi-directional or multi-directional network 16 to test unit 14 (step S100).

Test unit 14 stores the test program transmitted to it by management unit 12, preferably in flash memory 60d (step S110). Next, test unit 14 executes the stored test program, i.e., test unit 14 performs the filter test according to the test program or the test program instructions (step S120) and stores the test result, which can also include the system parameters stored in RAM 60b, preferably in fail-safe manner and preferably in flash memory 60d (step S130). Thereafter, the test result is transmitted to and received or detected by management unit 12 (step S150).

Management unit 12 can observe the progression of the filter test, i.e., it can read out and/or evaluate the current data from test unit 14 to provide or display it for the user on display device 36 and/or output device 38. Management unit 12 can also read out or output all the information related to the currently loaded test program of test unit 14.

Test unit 14 preferably preprocesses the test results such that management unit 12 can use and further process them essentially unchanged (step S140). In other words, test unit 14 converts units and translates numerical data into texts. Management unit 12 can then read out the preferably processed test data from test unit 14. The step of processing the test result can be provided before or after the step of storing the test results.

The inventive test device 10 is preferably configured as a validation-capable device, i.e., a validation of filter 18 to be tested can be performed simultaneously with the test.

The inventive test device 10 preferably provides additional functions, which are described below.

Management unit 12 comprises a so-called setup function to set a plurality of parameters for the entire test device 10 or for the filter tests. A subset of these parameters applies to test unit 14. In this connection, test unit 14 offers the following services or functions:

Test device 10 can furthermore be provided with a configuration function so that test unit 14 can be variously configured. To this end, management unit 12 sends the relevant configuration parameters to test unit 14. Management unit 12 can furthermore read out again the currently effective configuration parameters from test unit 14.

In addition, test device 10 preferably comprises a function test, which enables the user interactively to test the functional performance of components of test unit 14.

Test unit 14 further comprises functions for production and for the user, for instance, to test the functional performance of e.g., sensors and activators.

Test device 10 further comprises a calibration function for calibrating internal and the one external pressure sensors.

Test device 10 also comprises a cleaning function to clean test unit 14.

As described above, test unit 10 can be connected to an external PC or computer via PC interface 42. Through an update function, the operating program of test unit 14 can be replaced by another version.

Test unit 14 can preferably be controlled via hardware interface 82 by a programmable logic circuit or PLC, i.e., to start and stop filter tests and preferably to monitor them, i.e., the status of the filter test can be read out.

As may be seen from the foregoing description, communication between management unit 12 and the at least two test units 14 is preferably provided as a master-slave configuration. In particular, management unit 12 performs the function of the master, which actively assumes control and management of the at least two test units 14, and the at least two test units 14 are considered slaves, which perform a passive, executing function.

Communication between the management unit 12 and the at least two test units 14 preferably takes place via a defined protocol. The following Table 1 describes the preferably available communication services.

TABLE 1

| Application | Service/Result | Remarks |
| --- | --- | --- |
| Function control | Provide operating pressure status | Operating pressure outside required range and must be raised or lowered. |
| Function test | Load yes/no decision | Was an outflow of air from internal/external ventilation reported (yes/no). Result is transmitted to test unit 14 to collect test statuses. |
| Function test | Provide function test protocol | Management unit 12 requests status of all valve tests to generate a protocol. |
| Function test | Start function test | |
| Global | User abort/STOP | STOP key was pressed |
| Global | Provide software version | Software version is transmitted to test unit 14 |
| Global | Provide test unit status | Management unit 12 requests current status of a test unit 14 |
| Calibration | Load impressed current | The current impressed on the interface of the external pressure sensor was entered; it is transmitted to test unit 14 to calculate scaling/linearization |
| Calibration | Load reference | The pressure determined by the |

TABLE 1-continued

| Application | Service/Result | Remarks |
|---|---|---|
| | pressure | reference measuring device was entered, and transmitted to test unit 14 to calculate scaling/linearization |
| Calibration | Start adjustment (calibration) | |
| Calibration | Start verification | |
| Pressure gauge function | Provide actual measured pressure value | Management unit 12 requests the actual measured pressure value for continuous display. |
| Pressure gauge function | Provide calibration data | Management unit 12 requests data of the selected pressure sensor (internal/external) to display it |
| Pressure gauge function | Start pressure gauge function | |
| Cleaning | Supply purging pressure | Management unit 12 requests pressure during purging process |
| Cleaning | Start drying | |
| Cleaning | Load connection confirmation | Confirmation received that hoses are connected, test unit 14 can continue cleaning process |
| Cleaning | Load outflow confirmation | Confirmation received that liquid flowed out during flooding, test unit 14 can continue cleaning process |
| Cleaning | Start cleaning | |
| Management | Export configuration | Transmission of configuration parameters to management unit 12 |
| Management | Export test results | Transmission of test results to management unit 12 |
| Management | Export test program parameters | Transmission of test program parameters to management unit 12 |
| Management | Execute test program | Execution of currently loaded test program in test unit 14 |
| Management | Load configuration | Transmission of configuration parameters to test unit 14 |
| Management | Load test program | Transmission of test program parameters to test unit 14 |

The following Table 2 lists preferred communication functions, which management unit 12 can call to communicate as master with test units 14. Since at least two test units 14 are provided, the number or the address of test unit 14 to be addressed must be transmitted with each function call. Preferably, the communication functions internally implement a mechanism with transaction numbers to enable the individual functions to be uniquely assigned.

TABLE 2

| Function Name | Remarks |
|---|---|
| ClearError | Clears error in test unit 14 and readies unit for next test |
| GetAddress | Transmits address of the addressed test unit 14 to management unit 12 |
| GetCalibrationDate | Transmits the calibration date (time point) of the selected sensor to management unit 12 |
| GetCalibrationParameters | Transmits calibration data of the selected sensor to management unit 12 |
| GetCompleteStatus | Transmits extensive status information of test unit 14 to management unit 12 |
| GetConfiguration | Transmits the configuration data effective in test unit 14 to management unit 12 |
| GetDebugStatus | Transmits debug information to management unit 12 |
| GetFunctionTestResult | Transmits protocol of function test to management unit 12 |
| GetProgram | Transmits data of the test program active in test unit 14 to management unit 12 |
| GetRawList | Transmits raw measured data in numeric form to management unit 12 |
| GetResultList | Transmits measured result data in numeric form to management unit 12 |

TABLE 2-continued

| Function Name | Remarks |
|---|---|
| GetResultStrings | Transmits measured result data in text form to management unit 12 |
| GetSerialNo | Transmits serial no. of test unit 14 to management unit 12 |
| GetShortStatus | Transmits short status information of test unit 14 to management unit 12 |
| GetTime | Transmits current time of clock of test unit 14 to management unit 12 |
| GetVersion | Transmits software version of test unit to management unit |
| SetAddress | Sets address of test unit 14 |
| SetConfiguration | Transmits configuration data to test unit 14 |
| SetFloat | Transmits real number to test unit 14 |
| SetInteger | Transmits integer to test unit 14 |
| SetPLCEffect | Switches PLC interface effect ON/OFF |
| SetProgram | Transmits data of a test program to test unit 14 |
| SetTime | Sets clock in test unit 14 |
| SetTimeout | Sets communication timeout |
| SetTransaction | Starts a procedure in test unit 14 |
| StopTransaction | Aborts current procedure |

The invention also includes provision of a computer readable storage device with a computer program stored therein, which comprises suitable control commands, so that when the computer program is loaded onto a computer, a corresponding procedure according to the invention, or a preferred embodiment of the invention, can be controlled and executed.

The foregoing description and examples have been set forth merely to illustrate the invention and are not intended to be limiting. Since modifications of the disclosed embodiments incorporating the spirit and substance of the invention may occur to persons skilled in the art, the invention should be construed broadly to include all variations falling within the scope of the appended claims and equivalents thereof.

What is claimed is:

1. A test device for filter systems, said test device comprising:
    at least two test units, each comprising:
        a control unit for controlling the sequence of a test program or a test program instruction for one or more filter devices, and
        a pneumatic unit controlled by the control unit for providing and measuring pressures;
    a management unit for managing and controlling the at least two test units, wherein said management unit comprises:
        an input device for receiving user-specific inputs,
        an output device, and
        a processing unit for managing test programs or test program instructions and test results and for controlling the at least two test units; and
    signal links via a bi-directional or a multi-directional network for transmitting test program instructions and test results between the management unit and the at least two test units.

2. A test device according to claim 1, further comprising a data processing unit for processing data selected from the group consisting of test program instructions and test results.

3. A test device according to claim 1, further comprising a data storage device for storing at least one data selected from the group consisting of test program instructions and test results.

4. A test device according to claim 1, wherein the input device of the management unit comprises a keyboard or a touch screen.

5. A test device according to claim 1, wherein the output device of the management unit comprises a printer.

6. A test device according to claim 1, wherein the management unit further comprises a display device.

7. A test device according to claim 6, wherein the display device of the management unit is a monitor.

8. A test device according to claim 1, wherein the signal links between the management unit and the at least two test units comprise an electrical, optical, infrared or radio link.

9. A test device according to claim 1, wherein up to five test units are associated with the management unit.

10. A method for testing filter systems, said method comprising the steps of:
   transmitting at least one test program instruction from a management unit to at least one of at least two test units associated with the management unit;
   executing the at least one transmitted test program instruction in the at least one test unit to which the test program instruction was transmitted, whereby a test result is obtained; and
   recording the test result obtained by the at least one test unit in the management unit.

11. A method for testing filter systems, said method comprising the steps of:
   transmitting at least one test program instruction from a management unit to at least one of at least two test units associated with the management unit;
   executing the at least one transmitted test program instruction in the at least one test unit to which the test program instruction was transmitted, whereby a test result is obtained, and
   recording the test result obtained by the at least one test unit in the management unit;
   wherein the management unit communicates with the at least two test units essentially simultaneously.

12. A method according to claim 10, further comprising storing the at least one transmitted program instruction in one of the at least two test units.

13. A method according to claim 10, further comprising storing the test result in one of the at least two test units.

14. A method for testing filter systems, said method comprising the steps of:
   transmitting a plurality of test program instructions from a management unit to at least one of at least two test units associated with the management unit;
   detecting at least one of the test program instructions transmitted from the management unit to the at least one test unit;
   executing the at least one detected test program instruction in the at least one test unit to which the test program instructions were transmitted, whereby a test result is obtained, and
   transmitting the test result from the at least one test unit to the management unit.

15. A method according to claim 14, further comprising storing the at least one detected program instruction in one of the at least two test units.

16. A method according to claim 14, further comprising storing the test result in one of the at least two test units.

17. A method according to claim 16, further comprising processing the test result.

18. A computer readable storage device with a computer program for testing filter systems stored therein, said computer program comprising program sections with instructions for executing the method of claim 10.

19. A computer readable storage device with a computer program for testing filter systems stored therein, said computer program comprising program sections with instructions for executing the method of claim 14.

20. A test device for filter systems, said test device comprising:
   at least two test units, each comprising:
      a control unit for controlling the sequence of a test program or a test program instruction for one or more filter devices, and
      a pneumatic unit controlled by the control unit for providing and measuring pressures;
   a management unit for essentially simultaneously managing and controlling the at least two test units, wherein said management unit comprises:
      an input device for receiving user-specific inputs,
      an output device, and
      a processing unit for managing test programs or test program instructions and test results and for essentially simultaneously controlling the at least two test units; and
   signal links via a bi-directional or a multi-directional network for transmitting test program instructions and test results between the management unit and the at least two test units.

21. A method for testing filter systems, said method comprising the steps of:
   transmitting a plurality of test program instructions from a management unit to at least one of at least two test units associated with the management unit;
   detecting at least one of the test program instructions transmitted from the management unit to the at least one test unit;
   executing the at least one detected test program instruction in the at least one test unit to which the test program instructions were transmitted, whereby a test result is obtained, and
   transmitting the test result from the at least one test unit to the management unit,
   wherein the management unit communicates with the at least two test units essentially simultaneously.

* * * * *